(12) United States Patent
O'Dea et al.

(10) Patent No.: US 6,634,356 B1
(45) Date of Patent: Oct. 21, 2003

(54) CONTINUOUS POSITIVE AIRWAY PRESSURE CONTROLLER

(75) Inventors: John O'Dea, Galway (IE); John Denyer, Chichester (GB)

(73) Assignee: Caradyne (R&D) Limited, Parkmore West (IE)

( * ) Notice: Subject to any disclaimer, the term of this patent is extended or adjusted under 35 U.S.C. 154(b) by 0 days.

(21) Appl. No.: 09/786,373

(22) PCT Filed: Sep. 3, 1999

(86) PCT No.: PCT/IE99/00090

§ 371 (c)(1),
(2), (4) Date: May 21, 2001

(87) PCT Pub. No.: WO00/13731

PCT Pub. Date: Mar. 16, 2000

(30) Foreign Application Priority Data

Sep. 4, 1998 (IE) ................................................ S980739

(51) Int. Cl.[7] .......................... A61M 16/00; A62B 7/00; A62B 9/00
(52) U.S. Cl. ............................ 128/204.25; 128/204.18; 128/204.24; 128/205.11; 128/205.24
(58) Field of Search ....................... 128/205.12, 204.18, 128/204.21, 204.22, 204.23, 204.24, 204.25, 204.26, 205.11, 205.24

(56) References Cited

U.S. PATENT DOCUMENTS

| | | | | |
|---|---|---|---|---|
| 3,581,742 A | * | 6/1971 | Glenn | 128/204.25 |
| 4,022,202 A | * | 5/1977 | Price | 128/204.25 |
| 4,592,349 A | * | 6/1986 | Bird | 128/204.25 |
| 4,682,591 A | * | 7/1987 | Jones | 128/204.25 |
| 4,838,260 A | * | 6/1989 | Bird | 128/204.25 |
| 4,905,688 A | | 3/1990 | Vicenzi et al. | |
| 4,930,501 A | * | 6/1990 | Bird | 128/204.25 |
| 5,007,420 A | * | 4/1991 | Bird | 128/200.14 |
| 5,014,694 A | * | 5/1991 | DeVries | 128/205.24 |
| 5,165,398 A | * | 11/1992 | Bird | 128/204.25 |
| 5,605,148 A | * | 2/1997 | Jones | 128/205.11 |
| 5,752,506 A | * | 5/1998 | Richardson | 128/204.18 |

FOREIGN PATENT DOCUMENTS

| | | |
|---|---|---|
| DE | 35 37 507 A1 | 4/1987 |
| EP | 0691 137 A3 | 1/1996 |
| GB | 2174609 | 11/1986 |
| WO | WO 97/20592 | 6/1997 |

* cited by examiner

Primary Examiner—Weilun Lo
Assistant Examiner—Joseph F. Weiss, Jr.
(74) Attorney, Agent, or Firm—Swanson & Bratschun LLC (57) ABSTRACT

A CPAP controller that supplies oxygen enriched air to a respiratory circuit that utilizes a venturi-jet arrangement within a chamber, which enriches ambient air. Ambient air is drawn into the chamber by a primary oxygen flow source via an oxygen jet that directs oxygen into the venturi. Besides the conventional ability to adjust oxygen/air ratio via changes in the primary oxygen flow source's flow rate adjustment, the oxygen/air ratio may be altered by way of a secondary oxygen supply and its own flow control adjustment that is independent of the primary oxygen source and its adjustment mechanism. Hence the oxygen/air ratio may be adjusted independently of the primary oxygen source's flow rate. The controller further includes a pressure adjustment mechanism that allows the user to adjust pressure to the demand and/or need of the patient.

16 Claims, 7 Drawing Sheets

CONTINUOUS POSITIVE AIRWAY PRESSURE CONTROLLER

The present invention relates to a continuous positive airway pressure controller, and in particular, to such a controller for controlling the supply of oxygen to a respiratory circuit of a subject.

Such controllers supply oxygen or oxygen enriched air to a subject. Typically, the controller delivers the oxygen or oxygen enriched air to a respiratory circuit which feeds the oxygen or oxygen enriched air to the subject. In general, such controllers comprise a venturi mixer for mixing ambient air with oxygen for delivery to the subject. The oxygen, typically is derived from a pressurised source, such as a pressurised container, typically referred to as an oxygen bottle. In general, a primary supply of oxygen is delivered to the venturi mixer through a main jet from an inlet port of the controller. Air to be mixed with the oxygen is drawn into the venturi mixer by the primary oxygen issuing from the main jet, and an oxygen/air mix is delivered from an outlet port to the subject's respiratory circuit. A secondary supply of oxygen is delivered from the inlet port of the controller to the venturi mixer for enriching the air which is being drawn into the venturi mixer by the primary oxygen issuing from the main jet. In general, a flow regulator valve is provided for regulating the secondary oxygen supply to the venturi mixer for in turn regulating the proportion of oxygen in the oxygen/air mix from the venturi mixer. Typically, the proportion of oxygen in the oxygen/air mix may be varied within the range of 30% oxygen to 100% oxygen.

However, such controllers suffer from a number of disadvantages. Firstly, it is not possible to adjust the proportion of oxygen in the oxygen/air mix without altering the flow rate of the oxygen/air mix. To adjust the proportion of oxygen in the oxygen air mix, the flow regulator valve is adjusted for adjusting the secondary oxygen supply to the venturi mixer. This, thus, causes a change in pressure of the primary oxygen supply to the main jet, thereby altering the flow rate of the primary oxygen through the main jet, which in turn reduces the flow rate of the oxygen/air mix from the outlet port. This leads to significant problems, in that if it is desired to adjust the oxygen proportion of the oxygen/air mix a considerable number of adjustments are required subsequently in order to re-establish the desired flow rate with the desired oxygen proportion after adjustment of the oxygen/air mix ratio. A further disadvantage of such known controllers is that it is not possible to vary the flow rate of the oxygen/air mix without altering the oxygen/air mix ratio. Accordingly further adjustments are required to the flow rate of the secondary oxygen after a desired flow rate of the oxygen/air mix has been established. In many cases a series of alternate adjustments to the flow rate of the oxygen/air mix and the secondary oxygen are required before the desired flow rate and oxygen proportion of oxygen/air mix can be established.

There is therefore a need for a controller suitable for operating with a continuous positive airway pressure which address at least some of these problems.

The present invention is directed towards providing such a continuous positive airway pressure controller.

According to the invention, there is provided a continuous positive airway pressure controller for supplying a regulated oxygen/air mix to a respiratory circuit, the controller comprising a main oxygen inlet port for connecting to an oxygen supply source, a venturi mixing means located in a venturi accommodating chamber for blending oxygen and air to form the oxygen/air mix, a main jet means communicating with the main oxygen inlet port for delivering a primary oxygen supply through the venturi mixing means for drawing air from the venturi accommodating chamber into the venturi mixing means for blending air with the primary oxygen to form the oxygen/air mix, an air inlet to the venturi accommodation chamber for communicating the venturi accommodating chamber with ambient air, a secondary oxygen communicating means communicates the venturi accommodating chamber with the main oxygen inlet port for delivering a secondary oxygen supply into the venturi accommodating chamber for enriching the oxygen/air mix, and a main outlet port from the venturi mixing means for delivering the oxygen/air mix, wherein a secondary flow control means is provided for regulating the flow of oxygen through the secondary oxygen communicating means for varying the ratio of the oxygen to air of the oxygen/air mix delivered from the main outlet port, and a pressure regulating means is provided for maintaining the pressure of the oxygen being delivered to the main jet means and to the secondary flow control means substantially similar, and for varying the flow rate of the oxygen/air mix delivered from the main outlet port independently of the ratio of the oxygen to air of the oxygen/air mix.

In one embodiment of the invention a primary flow control means is provided for regulating the flow rate of the primary oxygen to the main jet means for accommodating different back pressures at the main outlet port caused by different operating pressures in respiratory circuits to which the main outlet port may be connected for delivering the oxygen/air mix. Preferably, the primary flow control means is fed from the pressure regulating means. Ideally, the primary flow control means is operable in a plurality of discrete configurations, which correspond with predetermined back pressures at the main outlet port caused by the different operating pressures in respiratory circuits to which the main outlet port may be connected.

In one embodiment of the invention the primary flow control means comprises a primary flow control valve.

In another embodiment of the invention a primary scale means is provided associated with the primary flow control means for facilitating selection of a desired configuration in which the primary flow control means is to operate.

Preferably, the secondary flow control valve is fed from the pressure regulating means.

In another embodiment of the invention a secondary scale means is provided associated with the secondary flow control means for facilitating selection of a desired operating configuration of the secondary flow control means for providing a desired ratio of oxygen to air of the oxygen/air mix.

In one embodiment of the invention the secondary flow control means comprises a secondary flow control valve.

In a further embodiment of the invention the pressure regulating means delivers a pressure regulated supply of oxygen to a main gallery from which the primary oxygen supply and the secondary oxygen supply are derived, the main gallery being sized for maintaining the oxygen pressure at the pressure set by the pressure regulating means throughout the main gallery.

In one embodiment of the invention the venturi mixing means comprises a venturi tube having an upstream inlet, the main jet means defining with the upstream inlet an annular opening which communicates the venturi tube with the venturi accommodating chamber for receiving air and the secondary oxygen supply into the venturi tube.

In another embodiment of the invention a back pressure monitoring means is provided for monitoring back pressure at the main outlet port.

Preferably, a first control means is provided for reading back pressure monitored by the back pressure monitoring means, and for controlling the primary flow control means in response to the back pressure monitored by the back pressure monitoring means for in turn accommodating different back pressures at the main outlet port caused by different operating pressures in respiratory circuits to which the main outlet port may be connected.

Advantageously, a second control means is provided for controlling the flow rate of the oxygen/air mix from the main outlet port for compensating for an excessive negative back pressure differential during an inspiration period of a breathing cycle of a subject, and for compensating for an excessive positive back pressure differential during an exhalation period of a breathing cycle, the second control means comprising a means for reading back pressure monitored by the back pressure monitoring means, and being responsive to the second control means determining that the negative and/or positive back pressure differentials during inspiration and/or exhalation are greater than respective predetermined reference negative and positive pressure differential values for controlling the pressure regulating means for varying the pressure of the oxygen for in turn varying the flow rate of the primary oxygen through the jet means for in turn varying the flow rate of the oxygen/air mix.

In one embodiment of the invention the second control means reads the back pressure monitored by the back pressure monitoring means at the main outlet port over a plurality of breathing cycles and determines the respective negative and positive average pressure differentials over the plurality of breathing cycles. Preferably, the second control means determines the respective average negative and positive pressure differentials over a predetermined number of breathing cycles. Advantageously, the second control means determines the respective average negative and positive pressure differentials over at least five breathing cycles. Ideally, the second control means averages the respective negative and positive back pressure differentials during the respective inspiration and exhalation periods over the plurality of breathing cycles.

In one embodiment of the invention the second control means controls the pressure regulating means for increasing the oxygen pressure for in turn increasing the flow rate of the oxygen/air mix from the main outlet port by a first predetermined increment in response to the average negative back pressure differential during the inspiration periods of the breathing cycles being greater than the reference negative pressure differential value.

In one embodiment of the invention each first predetermined increment of flow rate is at least 1 liter per minute. Preferably, each first predetermined increment of flow rate is at least 3 liters per minute. Ideally, each first predetermined increment of flow rate is approximately 5 liters per minute.

In another embodiment of the invention the second control means operates the pressure regulating means for decreasing the flow rate of the oxygen/air mix by a first predetermined decrement on the average negative back pressure differential during the inspiration period of the breathing cycles being less than the reference negative pressure differential value. Preferably, the value of each first predetermined decrement is less than the value of the first predetermined increment. Advantageously, the value of each first predetermined decrement is less than 3 liters per minute. Preferably, the value of each first predetermined decrement is less than 2 liters per minute. Ideally, the value of each first predetermined decrement is approximately 1 liter per minute.

In another embodiment of the invention the second control means operates the pressure regulating means for increasing the flow rate of the oxygen/air mix by a second predetermined increment on the average negative back pressure differential during the inspiration periods of the breathing cycles being greater than the reference negative pressure differential value after the flow rate of the oxygen/air mix has been reduced as a result of controlling the pressure regulating means for reducing the flow rate by one or more first predetermined decrements. Preferably, the value of each second predetermined increment is less than 3 liters per minute. Advantageously, the value of each second predetermined increment is less than 2 liters per minute. Ideally, the value of each second predetermined increment is approximately 1 liter per minute.

In a further embodiment of the invention the second control means controls the pressure regulating means for decreasing the flow rate of the oxygen/air mix from the main outlet port by a second predetermined decrement in response to the average positive back pressure differential during the exhalation period of the breathing cycles being greater than the reference positive pressure differential value. Preferably, each second predetermined decrement of flow rate is at least 1 liter per minute. Advantageously, each second predetermined decrement of flow rate is at least 3 liters per minute. Ideally, each second predetermined decrement of flow rate is approximately 5 liters per minute.

In a still further embodiment of the invention the second control means operates the pressure regulating means for increasing the flow rate of the oxygen/air mix by a third predetermined increment on the average positive back pressure differential during the exhalation periods of the breathing cycles being less than the reference positive pressure differential value. Preferably, the value of each third predetermined increment is less than the value of the second predetermined decrement. Advantageously, the value of each third predetermined increment is less than 3 liters per minute. Ideally, the value of each third predetermined incremented is less than 2 liters per minute, and more preferably, the value of each third predetermined increment is approximately 1 liter per minute.

In a further embodiment of the invention the second control means operates the pressure regulating means for decreasing the flow rate of the oxygen/air mix by a third predetermined decrement on the average positive back pressure differential during the exhalation periods of the breathing cycles being greater than the reference positive pressure differential value after the flow rate of the oxygen/air mix has been increased as a result of controlling the pressure regulating means for increasing the flow rate by one or more or the third predetermined increments. Preferably, the value of each third predetermined decrement is less than 3 liters per minute. Advantageously, the value of each third predetermined decrement is less than 2 liters per minute. Ideally, the value of each third predetermined decrement is approximately 1 liter per minute.

In a still further embodiment of the invention a supply pressure monitoring means is provided for monitoring the oxygen supply pressure from the oxygen supply source, and a switch means is provided responsive to the supply pressure monitoring means for isolating the first and second control means from a power supply means the oxygen supply pressure falling below a predetermined level. Preferably, the power supply means is a battery operated power supply means.

The advantages of the invention are many. The main advantage and most important advantage is that the ratio of oxygen to air of the oxygen/air mix from the main outlet port may be adjusted independently of the flow rate of the oxygen/air mix from the main outlet port, and vice versa. This important advantage is achieved by virtue of the fact that the flow rate of the oxygen/air mix is set and varied by the pressure regulating means, and accordingly, once the oxygen pressure in the controller has been set to give the desired flow rate of oxygen/air mix the oxygen pressure in the controller remains constant for a given flow rate of oxygen/air mix irrespective of alteration to the ratio of oxygen to air of the oxygen/air mix. Additionally, once the ratio of oxygen to air of the oxygen/air mix has been set by the secondary flow control means the flow rate of the oxygen/air mix can be varied by the pressure regulating means without affecting the ratio of oxygen to air of the oxygen/air mix due to the fact that the pressure regulating means maintains the oxygen pressure at the main jet means and the secondary flow control means similar after the oxygen pressure has been altered by the pressure regulating means, thereby leaving the ratio of oxygen to air in the oxygen/air mix unaltered.

By providing a monitoring means for monitoring back pressure at the main outlet port, and a first control means for controlling the primary control means in response to the back pressure monitored by the monitoring means the primary flow control means may be set to provide a flow rate of primary oxygen to the main jet means for in turn providing the oxygen/air mix at a flow rate to match the monitored back pressure. This aspect of the invention provides a particularly important advantage where it is likely that the pressure controller may be used with respiratory circuits which are to operate at respective different back pressures. It facilitates matching the flow rate of the oxygen/air mix with the back pressure at which the respiratory circuit is operating. It will be appreciated that the flow rate of the oxygen/air mix from the main outlet port would vary for different back pressures, and as the flow rate dropped as the back pressure increased the venturi mixing means would become less efficient, thereby possibly altering the ratio of the oxygen/air mix. By being able to compensate for different back pressures resulting from different respiratory circuits allows efficient operation of the controller with a wide range of respiratory circuits.

A further advantage of the invention is derived when the second control means is provided for controlling the flow rate of the oxygen/air mix from the main outlet port for compensating for an excessive pressure differential during inspiration and/or exhalation periods of a breathing cycle, since the provision of the second control means facilitates reduction of the back pressure differential to an optimised level during inspiration and exhalation periods.

The invention will be more clearly understood from the following description of some preferred embodiments thereof which are given by way of example only with reference to the accompanying drawings, in which.

Figure 1:
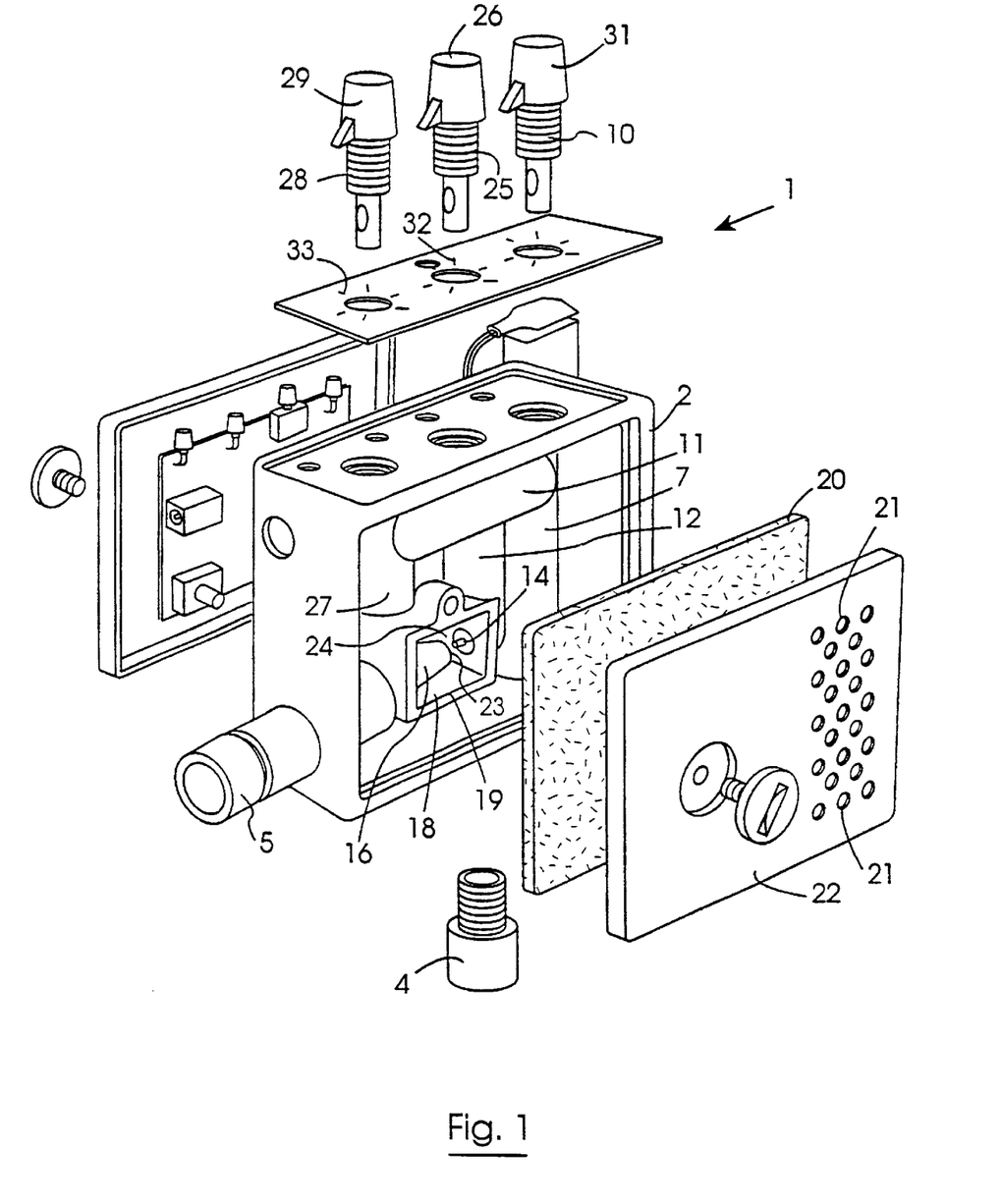
FIG. 1 is an exploded perspective view of a continuous positive airway pressure controller according to the invention.
Figure 2:
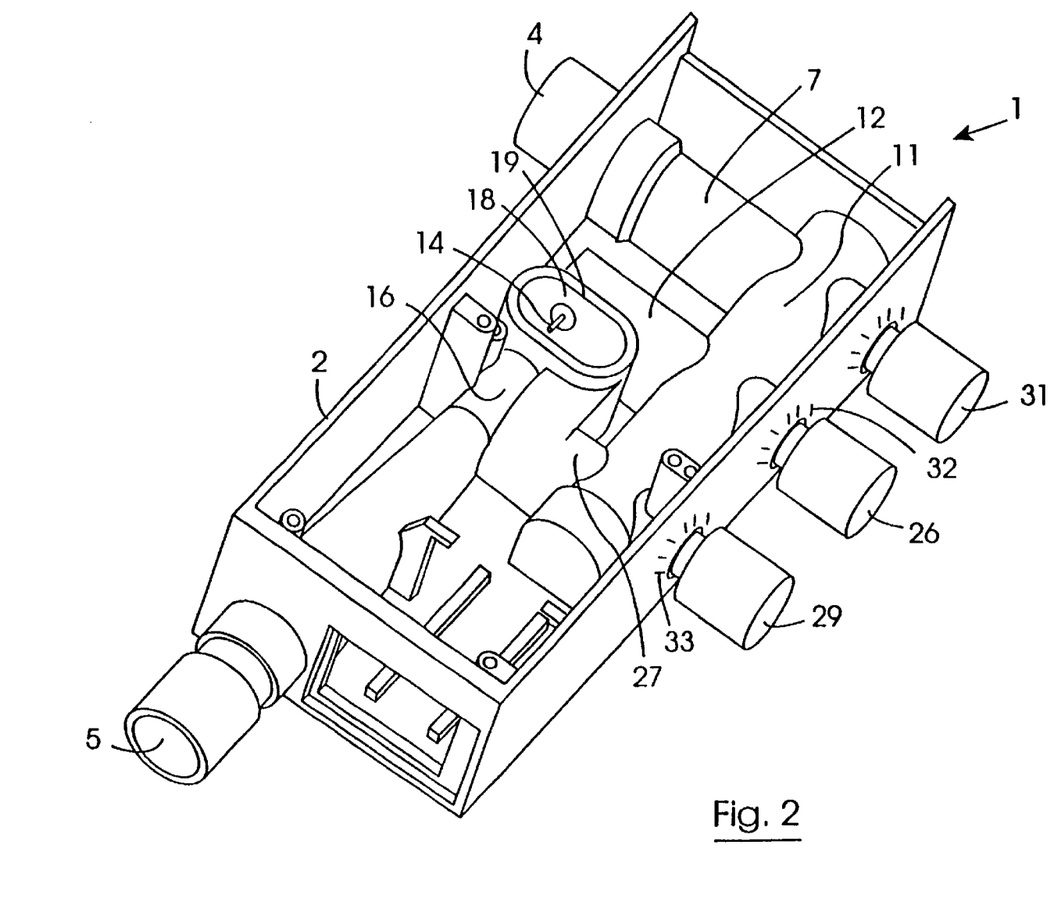
FIG. 2 is a perspective view of the controller of FIG. 1 with a portion of the controller removed.
Figure 3:
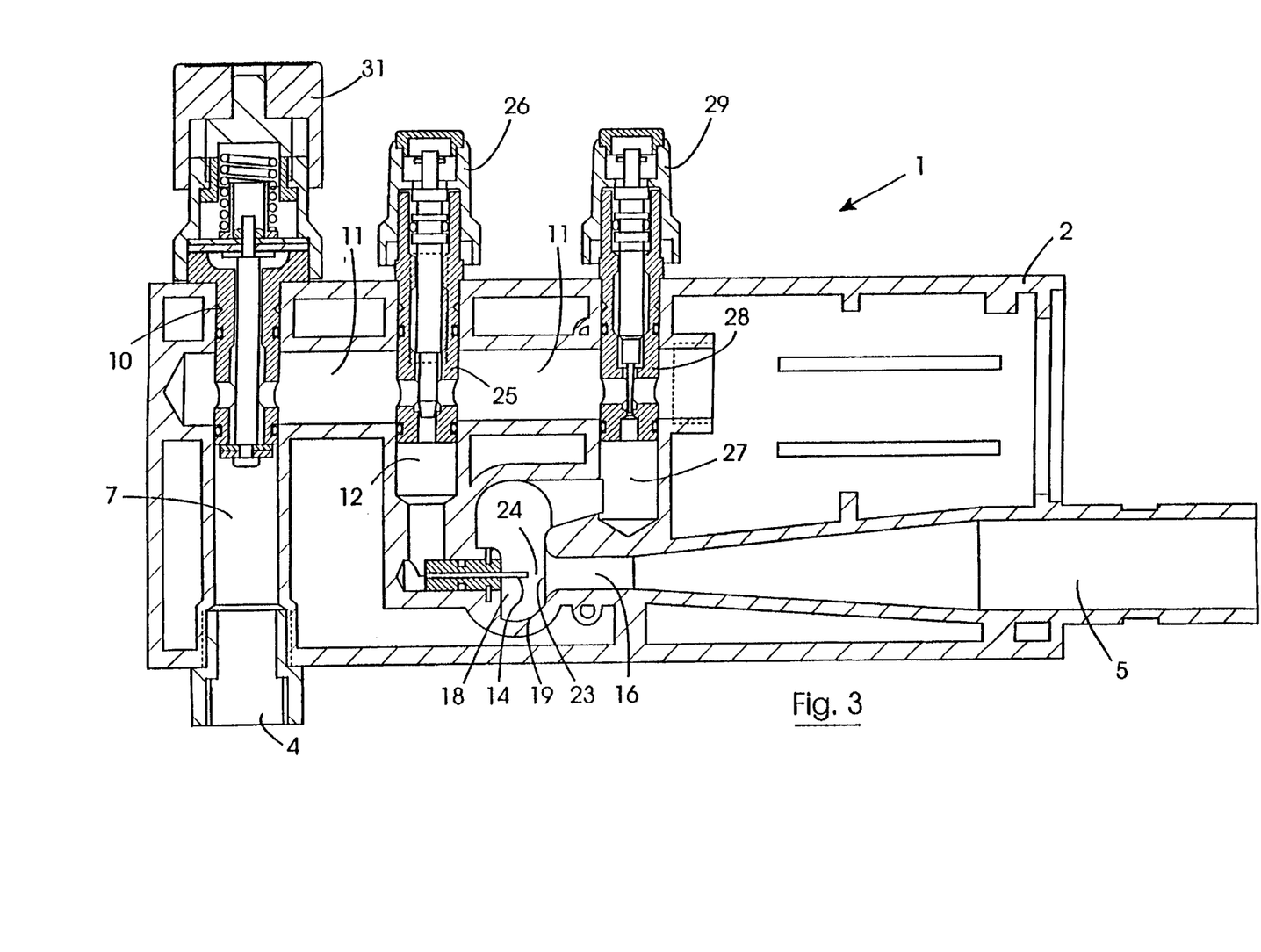
FIG. 3 is a transverse cross-sectional front elevational view of the controller of FIG. 1.

Referring to drawings and initially to FIGS. 1 to 3 there is illustrated a continuous positive airway pressure controller according to the invention indicated generally by the reference numeral 1 for supplying a regulated oxygen/air mix to a respiratory circuit (not shown) for supplying an enriched oxygen/air mix supply to a subject. The controller 1 regulates the flow rate of the oxygen/air mix being delivered to the respiratory circuit independently of the ratio of oxygen to air of the oxygen/air mix, and also regulates the ratio of oxygen to air in the oxygen/air mix independently of the flow rate. The controller 1 comprises a main body member 2 having a main oxygen inlet port 4 for receiving oxygen from a pressurised source, typically, an oxygen bottle (not shown), and a main outlet port 5 through which the regulated oxygen/air mix is delivered to the respiratory circuit (not shown) of the subject. The oxygen may also be derived from a pressure controlled oxygen supply provided on a manifold in a hospital ward or from any other suitable source.

A pressure regulating means, in this embodiment of the.invention provided by a pressure regulator 10 is located in an inlet gallery 7 which is fed from the main inlet port 4 for regulating the pressure of oxygen in the controller 1. The pressure regulator 10 by regulating the oxygen pressure in the controller 10 also regulates and controls the flow rate of the oxygen/air mix from the main outlet port 5 as will be described in more detail below. The oxygen, the pressure of which is regulated by the pressure regulator 10 is delivered from the regulator 10 into a main gallery 11. The main gallery 11 is sized for maintaining the pressure of the oxygen constant throughout the main gallery 11.

A primary oxygen supply is teed off from the main gallery 11 into a primary oxygen gallery 12 for providing a primary oxygen supply to a jet means, namely, a main jet 14 through which the primary oxygen supply is delivered to a venturi mixing means, namely, a venturi tube 16 where the primary oxygen supply is mixed with air for forming the oxygen/air mix. The venturi tube 16 terminates in the main outlet port 5 from which the oxygen/air mix is delivered to the respiratory circuit (not shown). The venturi mixing tube 16 extends from a venturi accommodating chamber 18 within which the main jet 14 is also located, and from which atmospheric air is drawn into the venturi tube 16 by the action of the primary oxygen supply from the main jet 14. An opening 19 in the venturi accommodating chamber 18 accommodates atmospheric air into the chamber 18. A filter 20 in the main body 2 filters the atmospheric air into the venturi accommodating chamber 18. A plurality of vent inlets 21 in a closure plate 22 of the main body 2 admit the atmospheric air to the filter 20 and in turn to the venturi accommodating chamber 18. An inlet end 23 of the venturi mixing tube 16 defines with the main jet 14 an annular opening 24 for communicating with the venturi accommodating chamber 18 and for receiving the atmospheric air therefrom.

A primary flow control means, namely, a primary flow control valve 25 controls the flow of primary oxygen into the primary gallery 12 for in turn varying the flow rate of primary oxygen through the main jet 14 for in turn varying the flow rate of the oxygen/air mix from the main outlet port 5 for accommodating different back pressures presented to the main outlet port 5 by different continuous positive airway pressure valves used in respiratory circuits to which the controller 1 may be connected. As will be described below adjustment of the primary flow control valve 25 for accommodating different back pressures does not affect the ratio of the oxygen to air of the oxygen air mix. A control knob 26 extending from the main body 2 is provided for operating the primary flow control valve 25. A secondary oxygen communicating means provided by a secondary oxygen supply gallery 27 is also teed off from the main gallery 11 for providing a secondary oxygen supply to the venturi accommodating chamber 18 for facilitating varying of the proportion of oxygen in the oxygen/air mix delivered from the main outlet port 5. A secondary flow control means comprising a secondary flow control valve 28 controls the secondary oxygen supply into the secondary oxygen supply gallery 27, for in turn permitting alteration of the proportion of oxygen in the oxygen/air mix. A control knob 29 extending from the main body 2 is provided for operating the secondary flow control valve 28.

A knob 31 extending from the main body 2 is provided for operating the pressure regulator 10.

A primary scale means, namely, a primary graduated scale 32 is provided adjacent the control knob 26 for indicating appropriate settings of the primary flow control valve 25 for matching the controller 1 to the different operating pressures of the respiratory circuits to which the controller 1 may be connected. In this embodiment of the invention four graduations are provided on the primary scale 32 which indicate four discrete settings of the primary flow control valve 25 which correspond to four conventional operating pressures of respiratory circuits. Typically, the four operating pressures of such respiratory circuits are 2.5 cms water gauge, 5 cms water gauge to 7.5 cms water gauge, 10 cms water gauge to 12.5 cms water gauge and 15 cms water gauge to 20 cms water gauge.

A secondary scale means, namely, a secondary graduated scale 33 is provided adjacent to the control knob 29 for indicating the amount of adjustment being made to the secondary flow control valve 28. The secondary scale 33 is graduated in percentages which indicates the percentage of oxygen of the oxygen/air mix from the main outlet port 5. In this embodiment of the invention the secondary scale 33 is graduated over a range of 30% oxygen to 100% oxygen.

In use, the main inlet port 4 of the controller 1 is connected to an oxygen source, typically, an oxygen bottle (not shown), or to a hospital oxygen supply which typically, is provided on an outlet manifold in a hospital ward, and which typically operates at approximately 4 bar. The main outlet port 5 is connected to the respiratory circuit (not shown) of the subject. The primary flow control valve 25 is set to the appropriate setting for matching the controller 1 to the operating pressure of the respiratory circuit to which the controller 1 is to be connected. The pressure regulator 10 is set to give the desired flow rate of the oxygen/air mix which typically is 60 liters per minute. The secondary flow control valve 28 is set to give the desired oxygen to air ratio of the oxygen/air mix.

Should it be desired to vary the oxygen to air ratio of the oxygen/air mix, the secondary flow control valve 28 is appropriately adjusted. Should it be desired to vary the flow rate of the oxygen/air mix from the main outlet port 5 appropriate adjustment is made to the pressure regulator 10.

The advantages of the invention are many. As discussed above the main and most important advantage of the invention is that by virtue of the fact that the flow rate of the oxygen/air mix from the main outlet port 5 is controlled by the pressure regulator 10 adjusting the flow rate of the oxygen/air mix does not alter the ratio of oxygen to air in the oxygen/air mix, which has been a problem of such controllers known heretofore. The reason for this is that the pressure regulator 10 maintains the oxygen pressure in the controller 1 constant once the desired flow rate has been established by setting the pressure to the appropriate value by the regulator. Accordingly, whether the pressure of the oxygen is increased or reduced by the pressure regulator 10 the pressure at which the primary oxygen is delivered to the main jet 14 and the pressure at which the secondary oxygen is delivered to the venturi accommodating chamber 18 is varied simultaneously, and thus, the pressure of the primary and secondary oxygen is always similar. Thus, the ratio of oxygen to air in the oxygen/air mix remains unaltered.

Additionally, operating the secondary control valve 28 for varying the proportion of oxygen in the oxygen/air mix does not affect the pressure of oxygen in the main gallery 11, and thus, the flow rate of primary oxygen through the main jet 14 remains unaltered, thereby, maintaining the flow rate of the oxygen/air mix through the main outlet port 5 constant even while the flow of the secondary oxygen is being varied by the secondary flow control valve 28.

Furthermore, since the pressure regulator 10 maintains the primary and secondary-oxygen supplies at similar pressures altering the flow rate of the primary oxygen by operation of the primary flow control valve 25 likewise does not alter the proportion of oxygen to air in the oxygen/air mix. Accordingly, once the desired oxygen/air mix proportion has been achieved the flow rate may be varied by either the pressure regulator 10 or the primary flow control valve 25 without altering the oxygen/air mix, and vice versa. Additionally, by altering the flow rate of primary oxygen by operating the primary flow control valve 25 for accommodating different back pressures does not alter the proportion of oxygen to air in the oxygen/air mix.

Figure 4:
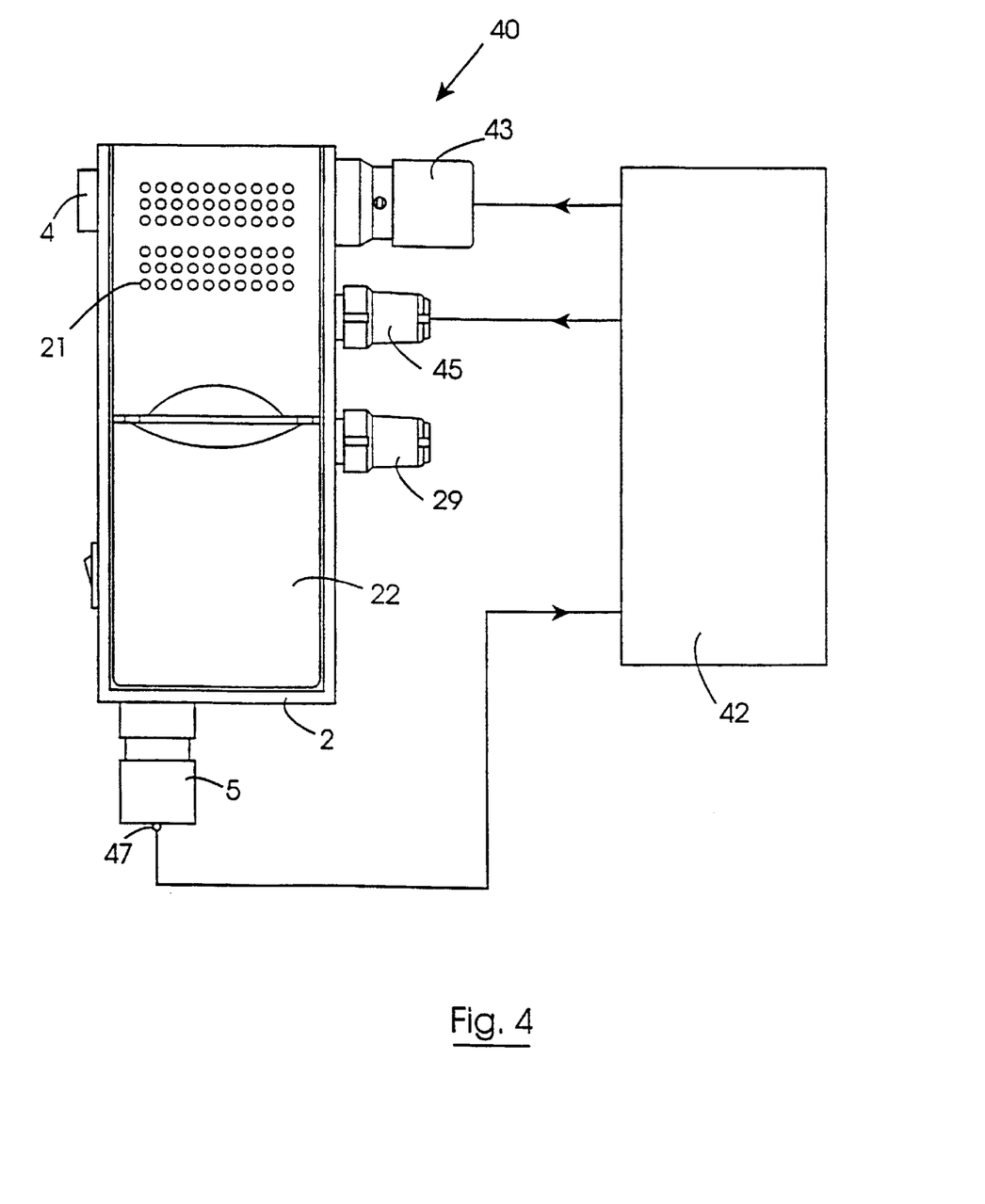
FIG. 4 is a block representation of an electronic control circuit of a controller also according to the invention of FIG. 1.

Referring now to FIG. 4 there is illustrated a controller 40 according to another embodiment of the invention, which is substantially similar to the controller 1 with the exception that an electronic control circuit 42 is provided for automatically controlling the pressure regulator 10 and the primary flow control valve 25. Components of the controller 40 which are illustrated and which are similar to those of the controller 1 are identified by the same reference numerals. In this embodiment of the invention the pressure regulator 10 is controlled by a solenoid controller 43 instead of by a control knob, and the primary flow control valve 25 is controlled by a solenoid controller 45 instead of by a control knob.

A back pressure monitoring means, namely, a pressure sensor 47 is located in the main outlet port 5 for monitoring back pressure at the outlet port 5 caused by the operating pressure and other pressure variables in the respiratory circuit (not shown) of the subject. The control circuit 42 controls the primary flow control valve 25 in response to the back pressure read by the pressure sensor 47 for setting the primary flow control valve 25 to the appropriate setting to match the operating pressure of the respiratory circuit. This, in general, requires a once off setting of the primary flow control valve 25 when the controller 1 is connected to the respiratory circuit. The primary flow control valve 25 is typically set to provide a flow rate of approximately 60 liters per minute. Additionally, the control circuit 42 controls the pressure regulator 10 for minimising pressure fluctuations, in other words, pressure differentials in the back pressure monitored by the pressure sensor 47 which result during inspiration and exhalation periods of a breathing cycle.

Figure 5:
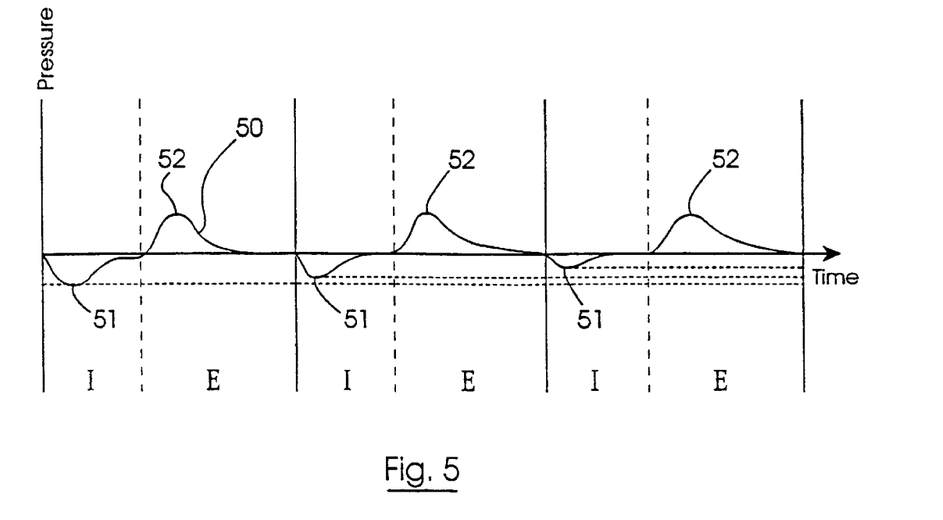
FIG. 5 is a graphical representation of three breathing cycles of a subject using the controller of FIG. 4.
Figure 6:
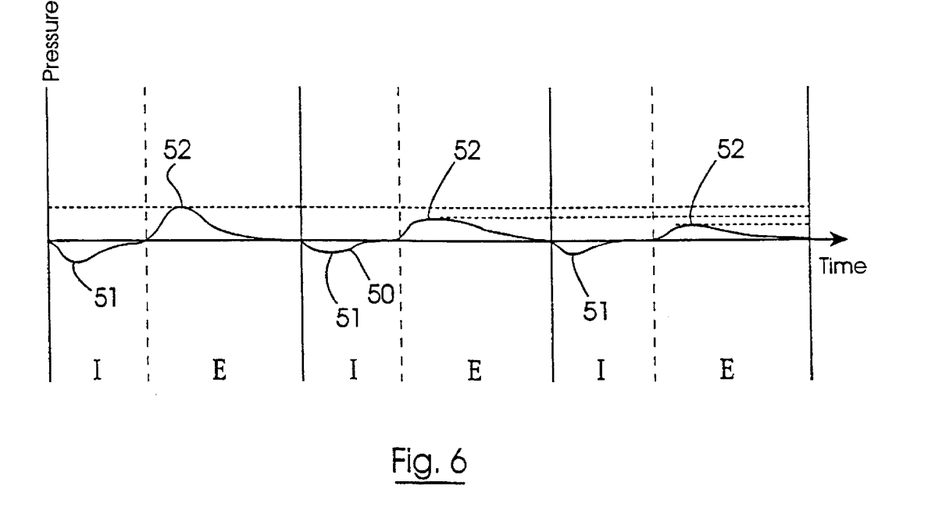
FIG. 6 is a view similar to FIG. 5 also illustrating three breathing cycles of a subject using the controller of FIG. 4.

Referring in particular to FIGS. 5 and 6 graphs 50 illustrate typical pressure fluctuations in the back pressure during three breathing cycles of the subject. Pressure is plotted on the Y-axis while time is plotted on the X-axis. The parts of the graphs 50 identified by the letter I show the back pressure fluctuation during inspiration periods of the respective breathing cycles, and the parts of the graphs 50 indicated by the letter E indicate the back pressure fluctuation during exhalation periods of the respective breathing cycles. The graph 50 of FIG. 5 illustrates the results which can be achieved by adjusting the pressure controller 10 to incrementally increase the flow rate of the oxygen/air mix for reducing the negative pressure differential 51 during inspiration. In this case the pressure regulator 10 is operated initially for gradually increasing the flow rate of the oxygen/air mix, thereby reducing the negative pressure differential 51 during the inspiration periods of the breathing cycles. In FIG. 6 the pressure regulator 10 is adjusted for decrementally reducing the flow rate of the oxygen/air mix for in turn reducing the positive pressure differential 52 during the exhalation period of the breathing cycles.

Referring initially to FIG. 5, the control circuit 42 comprises a microprocessor which is programmed to control the pressure regulator 10 according to the following algorithm for reducing the negative pressure differential 51 in the inspiration periods of the breathing cycles. Initially, the control circuit 42 controls the pressure regulator 10 for reducing the negative pressure differential 51 during the inspiration periods of the breathing cycles. The control circuit 42 reads the pressure sensor 47 for five breathing cycles and determines the average negative pressure differential during the five inspiration periods. If the average negative pressure differential is greater than a predetermined reference negative pressure differential value the control circuit 42 operates the pressure regulator for increasing the oxygen pressure, for in turn increasing the flow rate of the oxygen/air mix by a first predetermined increment, which in this embodiment of the invention is approximately 5 liters per minute. After a further five breathing cycles and averaging the negative pressure differential during the inspiration periods, if the average negative pressure differential is still greater than the reference negative pressure differential value, the control circuit 42 again controls the pressure regulator 10 for increasing the flow rate of oxygen/air mix by a further first predetermined increment of 5 liters per minute. This procedure continues until the average negative pressure differential during the inspiration periods is equal to or less than the reference negative pressure differential value. Once the average negative pressure differential during the inspiration periods is equal to the reference negative pressure differential value, no further action is required. If the average negative pressure differential during the inspiration periods is less than the reference negative pressure differential value, then the control circuit 42 operates the pressure regulator 10 for decreasing the oxygen pressure for in turn decreasing the flow rate by a first predetermined decrement which in this embodiment of the invention is approximately 1 liter per minute. This procedure continues until the average negative pressure differential in the inspiration period is at or greater than the reference negative pressure differential value. In the event that the average negative pressure differential during the inspiration periods is greater than the reference negative pressure differential value the control circuit 42 again operates the pressure regulator 10 for increasing the oxygen/air mix flow rate by a second predetermined increment of approximately 1 liter per minute. No further adjustment is carried out for adjusting the average negative pressure differential unless the average negative pressure differential during the inspiration periods should again exceed the reference negative pressure differential value.

Referring now to FIG. 6, after the negative pressure differential during the inspiration periods of the breathing cycles has been adjusted the pressure controller 10 is then operated by the control circuit 42 for bringing the positive pressure differential 52 during the exhalation periods of the breathing cycles to a predetermined reference positive pressure differential value. This is achieved in similar fashion to that already described for controlling the negative pressure differential during the inspiration periods, with the exception that, should the average positive pressure differential during the exhalation periods of five breathing cycles exceed the reference positive pressure differential value, instead of initially increasing the flow rate of the oxygen/air mix, the pressure regulator 10 is initially controlled for decreasing the oxygen/air mix by a second predetermined decrement of approximately 5 liters per minute, for reducing the positive pressure differential during the exhalation periods. Should the positive pressure differential during the exhalation periods be adjusted so that the average positive pressure differential is less than the reference positive pressure differential value during the exhalation periods, the pressure regulator 10 is operated for increasing the oxygen/air mix flow rate by a third predetermined increment of approximately 1 liter per minute. Similarly should the average positive pressure differential during the exhalation periods during this phase of adjustment exceed the reference positive pressure differential value, the pressure regulator 10 is further operated for decreasing the oxygen/air mix flow rate by a third predetermined decrement of approximately 1 liter per minute. No further adjustment is carried out for adjusting the average positive pressure differential unless the average positive pressure differential during the exhalation periods of the breathing cycles should become greater than the reference positive pressure differential value, in which case, the adjustment process is commenced again.

It will be appreciated that the adjustment of negative and positive pressure differentials during inspiration and exhalation requires some level of optimisation since a decrease in the positive pressure differential during exhalation will cause an increase in the negative pressure differential during inspiration and vice versa. Typically, the predetermined reference negative and positive pressure differential values are similar, and preferably are set at 1 cm water gauge, approximately.

Figure 7:
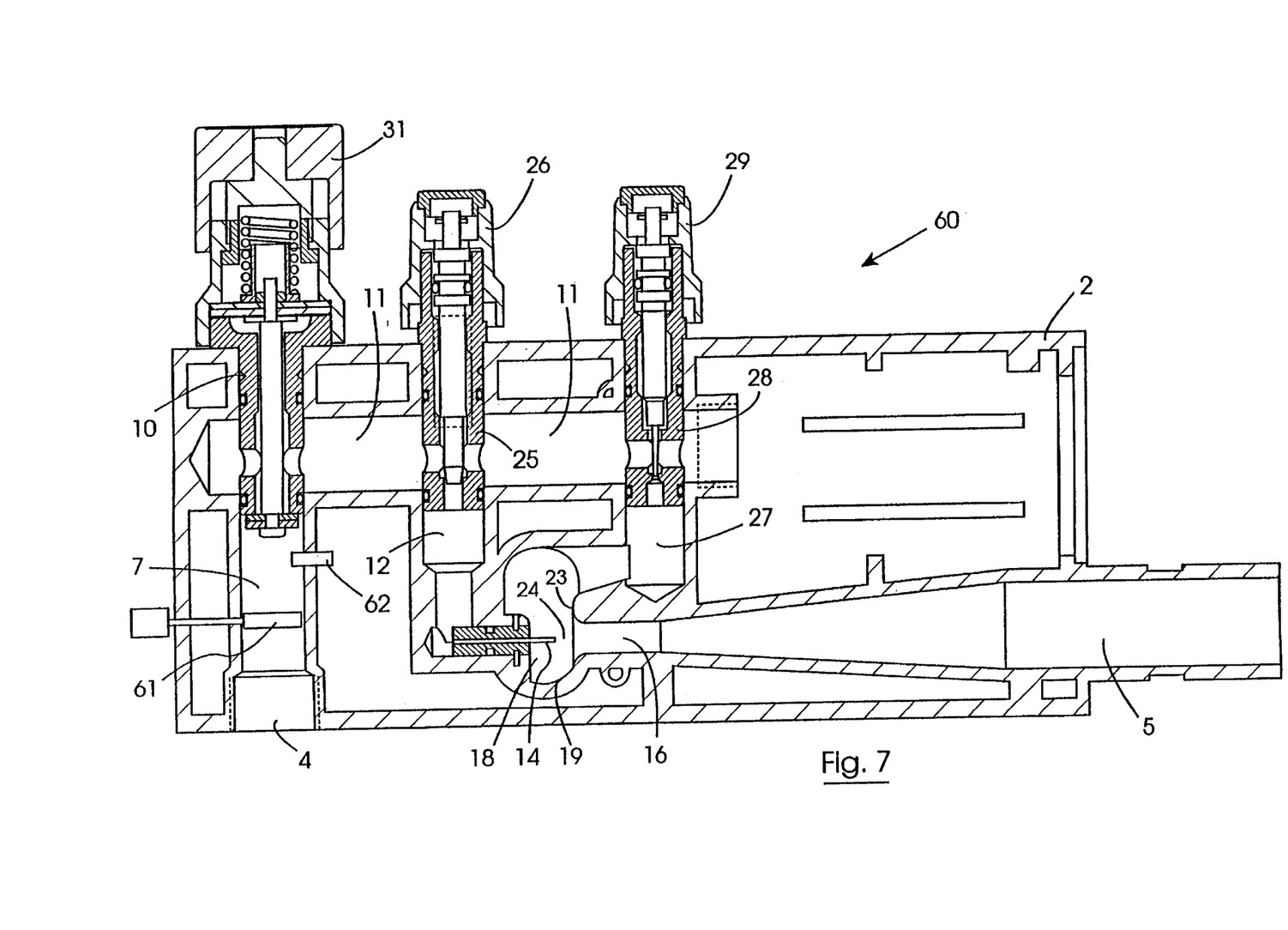
FIG. 7 is a view similar to FIG. 3 of a continuous positive airway pressure controller according to another embodiment of the invention, and 11
Figure 8:
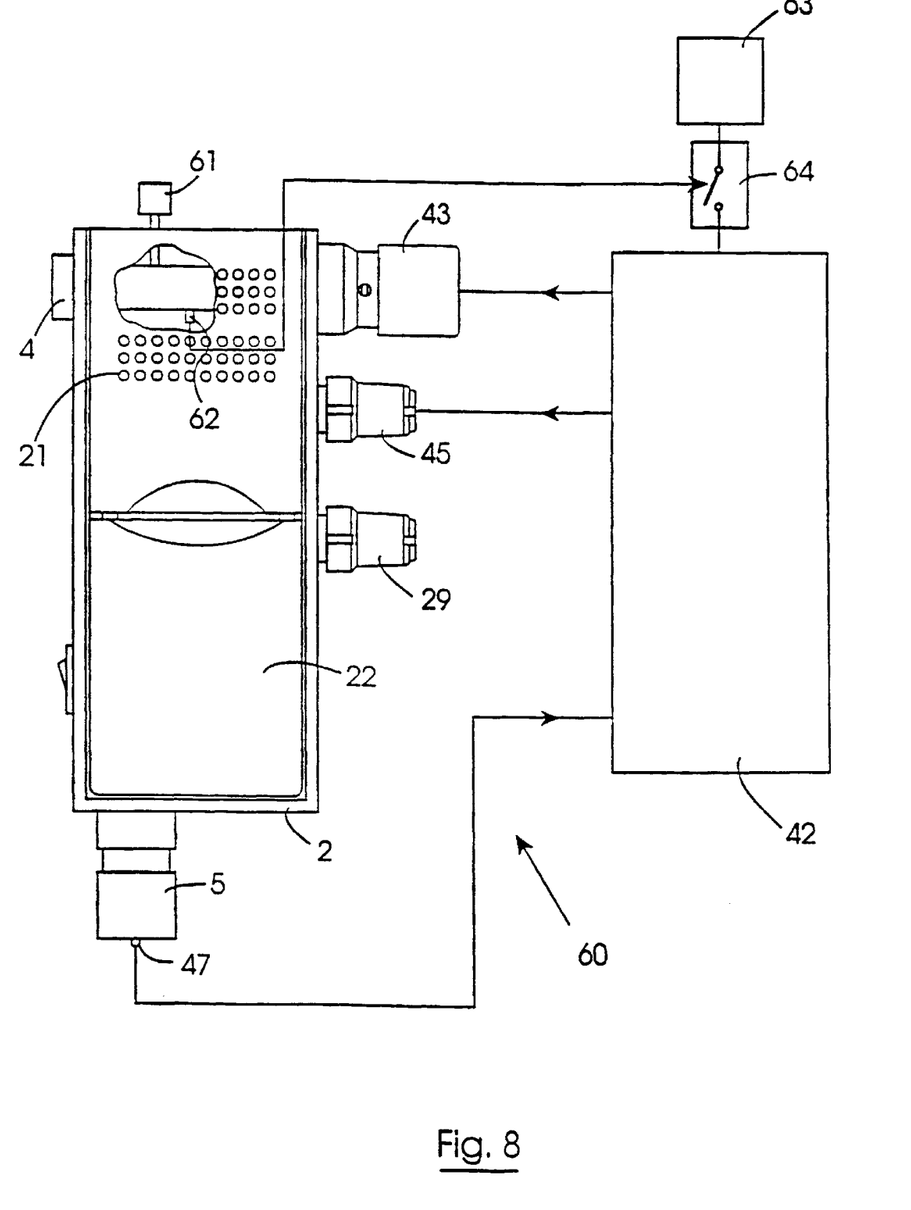
FIG. 8 is a view similar to FIG. 4 of a block representation of an electronic control circuit of the continuous positive airway pressure controller of FIG. 7.

Referring now to FIGS. 7 & 8 there is illustrated a continuous positive airway pressure controller according to another embodiment of the invention which is indicated generally by the reference numeral 60. The controller 60 is substantially similar to the controller 40 and the controller 1, and similar components are identified by the same reference numerals. The main difference between the controller 60 and the controllers 1 and 40 is that a hand operated isolating valve 61 for isolating the controller 60 from an oxygen supply is located in the inlet gallery 7. A supply pressure monitoring means, namely, a pressure sensor 62 is located in the inlet gallery 7 downstream of the isolating valve 61 for monitoring the pressure of the supply oxygen for determining if the isolating valve 61 has isolated the controller 60 from the oxygen supply. A power supply circuit 63 supplies the electronic control circuit 42 with electrical power through an electrical isolating switch 64. The isolating switch 64 is responsive to the pressure sensor 62 detecting the absence of supply pressure in the gallery 7 for operating the isolating switch 64 for in turn isolating the electronic control circuit 42 from the power supply circuit 63. Accordingly, when the controller 60 is isolated from the oxygen supply, the electronic control circuit 42 is isolated from the power supply circuit 63 for conserving electrical power in the power supply circuit 63. Typically, it is envisaged that the power supply circuit 63 will include a battery (not shown).

It is envisaged that the pressure sensor 62 and the isolating switch 64 may be provided as a single integral unit, such as, for example, a pressure operated electrical switch. It is also envisaged that the pressure sensor 62 may be located downstream of the pressure regulator 10.

It will be appreciated that the pressure regulator and the primary flow control valve in the embodiments of the invention described with reference to FIGS. 4 and 8 may be controlled by any other suitable electronic or electrical control means, besides a solenoid controller.

What is claimed is:

1. A continuous positive airway pressure controller (1,40, 60) for supplying a regulated oxygen/air mix to a respiratory circuit, the controller (1,40,60) comprising a main oxygen inlet port (4) for connecting to an oxygen supply source, a venturi mixing means (16) located in a venturi accommodating chamber (18) for blending oxygen and air to form the oxygen/air mix, a main jet means (14) communicating with the main oxygen inlet port (4) for delivering a primary oxygen supply through the venturi mixing means (16) for drawing air from the venturi accommodating chamber (18) into the venturi mixing means (16) for blending air with the primary oxygen to form the oxygen/air mix, an air inlet (19) to the venturi accommodation chamber (18) for communicating the venturi accommodating chamber (18) with ambient air, a secondary oxygen communicating means (27) communicates the venturi accommodating chamber (18) with the main oxygen inlet port (4) for delivering a secondary oxygen supply into the venturi accommodating chamber (18) for enriching the oxygen/air mix, and a main outlet port (5) from the venturi mixing means (16) for delivering the oxygen/air mix, characterised in that a secondary flow control means (28) is provided for regulating the flow of oxygen through the secondary oxygen communicating means (27) for varying the ratio of the oxygen to air of the oxygen/air mix delivered from the main outlet port (5), and a pressure regulating means (10) is provided for maintaining the pressure of the oxygen being delivered to the main jet means (14) and to the secondary flow control means (28) substantially similar, and for varying the flow rate of the oxygen/air mix delivered from the main outlet port (5) independently of the ratio of the oxygen to air of the oxygen/air mix.

2. A controller as claimed in claim 1 characterised in that the secondary flow control valve (28) is fed from the pressure regulating means (10), and preferably, a secondary scale means (33) is provided associated with the secondary flow control means (28) for facilitating selection of a desired operating configuration of the secondary flow control means (28) for providing a desired ratio of oxygen to air of the oxygen/air mix, and preferably, the secondary flow control means (28) comprises a secondary flow control valve (28).

3. A controller as claimed in claim 1 characterised in that the pressure regulating means (10) delivers a pressure regulated supply of oxygen to a main gallery (11) from which the primary oxygen supply and the secondary oxygen supply are derived, the main gallery (11) being sized for maintaining the oxygen pressure at the pressure set by the pressure regulating means (10) throughout the main gallery (11), and preferably, the venturi mixing means (16) comprises a venturi tube (16) having an upstream inlet (23), the main jet means (14) defining with the upstream inlet (23) an annular opening (24) which communicates the venturi tube (16) with the venturi accommodating chamber (18) for receiving air and the secondary oxygen supply into the venturi tube (16).

4. A controller as claimed in claim 1 characterised in that a primary flow control means (25) is provided for regulating the flow rate of the primary oxygen to the main jet means (14) for accommodating different back pressures at the main outlet port (5) caused by different operating pressures in respiratory circuits to which the main outlet port (5) may be connected for delivering the oxygen/air mix.

5. A controller as claimed in claim 4 characterised in that the primary flow control means (25) is fed from the pressure regulating means (10), and preferably, the primary flow control means (25) is operable in a plurality of discrete configurations, which correspond with predetermined back pressures at the main outlet port (5) caused by the different operating pressures in respiratory circuits to which the main outlet port (5) may be connected, and advantageously, the primary flow control means (25) comprises a primary flow control valve (25).

6. A controller as claimed in claim 4, characterised in that a primary scale means (32) is provided associated with the primary flow control means (25) for facilitating selection of a desired configuration in which the primary flow control means (25) is to operate.

7. A controller as claimed in claim 4 characterised in that a back pressure monitoring means (47) is provided for monitoring back pressure at the main outlet port (5), and preferably, a first control means (42) is provided for reading back pressure monitored by the back pressure monitoring means (47), and for controlling the primary flow control means (25) in response to the back pressure monitored by the back pressure monitoring means (47) for in turn accommodating different back pressures at the main outlet port (5) caused by different operating pressures in respiratory circuits to which the main outlet port (5) may be connected.

8. A controller as claimed in claim 7 characterised in that a supply pressure monitoring means (62) is provided for monitoring the oxygen supply pressure from the oxygen supply source, and a switch means (64) is provided responsive to the supply pressure monitoring means (62) for isolating the first and second control means (42) from a power supply means (63) the oxygen supply pressure falling below a predetermined level, and preferably, the power supply means (63) is a battery operated power supply means.

9. A controller as claimed in claim 7 characterised in that a second control means (42) is provided for controlling the flow rate of the oxygen/air mix from the main outlet port (5) for compensating for an excessive negative back pressure differential during an inspiration period of a breathing cycle of a subject, and for compensating for an excessive positive back pressure differential during an exhalation period of a breathing cycle, the second control means (42) comprising a means for reading back pressure monitored by the back pressure monitoring means (47), and being responsive to the second control means (42) determining that the negative and/or positive back pressure differentials during inspiration and/or exhalation are greater than respective predetermined reference negative and positive pressure differential values for controlling the pressure regulating means (10) for varying the pressure of the oxygen for in turn varying the flow rate of the primary oxygen through the jet means (14) for in turn varying the flow rate of the oxygen/air mix, and preferably, the second control means (42) reads the back pressure monitored by the back pressure monitoring means (47) at the main outlet port (5) over a plurality of breathing cycles and determines the respective average negative and positive pressure differentials over the plurality of breathing cycles, and advantageously, the second control means (42) determines the respective average negative and positive pressure differentials over a predetermined number of breathing cycles, and preferably, the second control means (42) determines the respective average negative and positive pressure differentials over at least five breathing cycles.

10. A controller as claimed in claim 9 characterised in that the second control means (42) averages the respective negative and positive back pressure differentials during the respective inspiration and exhalation periods over the plurality of breathing cycles, and preferably, the second control means (42) controls the pressure regulating means (10) for increasing the oxygen pressure for in turn increasing the flow rate of the oxygen/air mix from the main outlet port (5) by a first predetermined increment in response to the average negative back pressure differential during the inspiration periods of the breathing cycles being greater than the reference negative pressure differential value, and preferably, each first predetermined increment of flow rate is at least 1 liter per minute, and advantageously, each first predetermined increment of flow rate is at least 3 liters per minute, and preferably, each first predetermined increment of flow rate is approximately 5 liters per minute.

11. A controller as claimed in claim 9 characterised in that the second control means (42) operates the pressure regulating means (10) for decreasing the flow rate of the oxygen/air mix by a first predetermined decrement on the average negative back pressure differential during the inspiration period of the breathing cycles being less than the reference negative pressure differential value, and preferably, the value of each first predetermined decrement is less than the value of the first predetermined increment.

12. A controller as claimed in claim 11 characterised in that the value of each first predetermined decrement is less than 3 liters per minute, and preferably, the value of each first predetermined decrement is less than 2 liters per minute, and advantageously, the value of each first predetermined decrement is approximately 1 liter per minute.

13. A controller as claimed in claim 9 characterised in that the second control means (42) operates the pressure regulating means (10) for increasing the flow rate of the oxygen/air mix by a second predetermined increment on the average negative back pressure differential during the inspiration periods of the breathing cycles being greater than the reference negative pressure differential value after the flow rate of the oxygen/air mix has been reduced as a result of controlling the pressure regulating means for reducing the flow rate by one or more first predetermined decrements, and advantageously, the value of each second predetermined increment is less than 3 liters per minute, and preferably, the value of each second predetermined increment is less than 2 liters per minute, and advantageously, the value of each second predetermined increment is approximately 1 liter per minute.

14. A controller as claimed in claim 9 characterised in that the second control means (42) controls the pressure regulating means (10) for decreasing the flow rate of the oxygen/air mix from the main outlet port by a second predetermined decrement in response to the average positive back pressure differential during the exhalation period of the breathing cycles being greater than the reference positive pressure differential value, and advantageously, each second predetermined decrement of flow rate is at least 1 liter per minute, and preferably, each second predetermined decrement of flow rate is at least 3 liters per minute, and advantageously, each second predetermined decrement of flow rate is approximately 5 liters per minute.

15. A controller as claimed in claim 9 characterised in that the second control means (42) operates the pressure regulating means (10) for increasing the flow rate of the oxygen/air mix by a third predetermined increment on the average positive back pressure differential during the exhalation periods of the breathing cycles being less than the reference positive pressure differential value, and preferably, the value of each third predetermined increment is less than the value of the second predetermined decrement, and advantageously, the value of each third predetermined increment is less than 3 liters per minute, and preferably, the value of each third predetermined incremented is less than 2 liters per minute, and preferably, the value of each third predetermined increment is approximately 1 liter per minute.

16. A controller as claimed in claim 9 characterised in that the second control means (42) operates the pressure regulating means (10) for decreasing the flow rate of the oxygen/air mix by a third predetermined decrement on the average positive back pressure differential during the exhalation periods of the breathing cycles being greater than the reference positive pressure differential value after the flow rate of the oxygen/air mix has been increased as a result of controlling the pressure regulating means for increasing the flow rate by one or more third predetermined increments, and preferably, the value of each third predetermined decrement is less than 3 liters per minute, and preferably, the value of each third predetermined decrement is less than 2 liters per minute, and advantageously, the value of each third predetermined decrement is approximately 1 liter per minute.

* * * * *